United States Patent [19]
Vaitekunas et al.

[11] Patent Number: 5,807,285
[45] Date of Patent: Sep. 15, 1998

[54] MEDICAL APPLICATIONS OF ULTRASONIC ENERGY

[75] Inventors: Jeffrey Joseph Vaitekunas, West Chester; Ronald David Adams, Wyoming, both of Ohio

[73] Assignee: Ethicon-Endo Surgery, Inc., Cincinnati, Ohio

[21] Appl. No.: 624,238

[22] Filed: Mar. 29, 1996

Related U.S. Application Data

[63] Continuation of Ser. No. 292,711, Aug. 18, 1994, abandoned.

[51] Int. Cl.$^6$ .................................................. A61B 17/22
[52] U.S. Cl. ............................................................ 601/2
[58] Field of Search ........................... 601/2; 128/660.03, 128/662.03; 604/22; 607/50, 51

[56] References Cited

U.S. PATENT DOCUMENTS

| | | | |
|---|---|---|---|
| 5,180,363 | 1/1993 | Idemoto et al. | 310/316 |
| 5,326,342 | 7/1994 | Pflueger et al. | 601/4 |
| 5,437,606 | 8/1995 | Tsukamoto et al. | 601/2 |

FOREIGN PATENT DOCUMENTS

| | | | |
|---|---|---|---|
| 4212338 | 8/1992 | Japan | 601/2 |
| 3016646 | 9/1993 | WIPO | 601/2 |

OTHER PUBLICATIONS

Christensen, D.A., *Ultrasonic Bioinstrumentation*, Chapter 5: "Transducers, Beam Patters, and Resolution", John Wiley & Sons, pp. 90–95.
Zemanek, "Beam Behavior within the Nearfield of a Vibrating Piston," *The Journal of the Acoustical Society of America*, Aug. 24, 1970, p. 181.
Brochure for Sonotherm 1000 Therapy System, Labthermics Technologies, Inc.—4 pages.
Ziskin et al., "Ultrasonic Exposimetry," CRC Press, pp. 20–22, 37, 50–52, 82 and 98.
Vujaskovic et al., "Effects of Intraoperative Hyperthermia or Peripheral Nerves," pp.282 and 284–285.
Vakil et al., "Transiet Acoustic Cavitation in Gallstone Fragmentation: A Study of Gallstones Fragmented in Vivo," *Ultrasound in Med. & Biol.*, vol. 19, No. 4, 1993, pp. 331–342.
Apfel, R.E., "Acoustic Cavitation: A Possible Consequence of Biomedical Uses of Ultrasound," *Br. J. Cancer*, 45, Suppl. V, 1982, pp. 140–146.
Dyson, M., "Non–Thermal Cellular Effects of Ultrasound," *Br. J. Cancer*, 45, Suppl. V, 1982, pp. 165–171.
Hue, A., "Technical Aspects of Ultrasonic Aspirators," Soring Medizintechnik GmbH, 2 pages.
Hurst et al., complete title is unknown, *Fertility and Sterility*, vol. 58, No. 2, Aug. 1992, pp. 444–448.
Gleeson et al., "A Morphological Study of the Effect of the Cavitron Ultrasonic Surgical Aspirator System Near Human Peripheral Nerves," *Arch Otolaryngol Head Neck Surg*, vol. 113, May 1987, pp. 530–532.
Fischer et al., "The Use of High–Frequency Ultrasound for the Dissection of Small–Diameter Blood Vessels and Nerves," Little Brown and Company, 1992, pp. 326–330.
Gleeson et al., "The cavitron ultrasonic aspirator system. An anatomical and physiological study of the effect of its use on the rat facial nerve," *Clin. Otolaryngol*, 11, 1986, pp. 177–187.
Lele, P., "Effects of Focused Ultrasonic Radiation on Peripheral Nerve, with Observations on Local Heating," Reprinted from *Experimental Neurology*, vol. 3, No. 1, Jul. 1963, pp. 47–79.

*Primary Examiner*—Brian L. Casler

[57] ABSTRACT

Ultrasonic energy is used to cause a given nerve to become dysfunctional without substantially damaging tissues surrounding or associated with the nerve. A nerve to be treated is placed in the near field or evanescent field of an ultrasonic wave front emitted by an appropriately formed contact or non-contact ultrasonic probe or transducer.

6 Claims, 5 Drawing Sheets

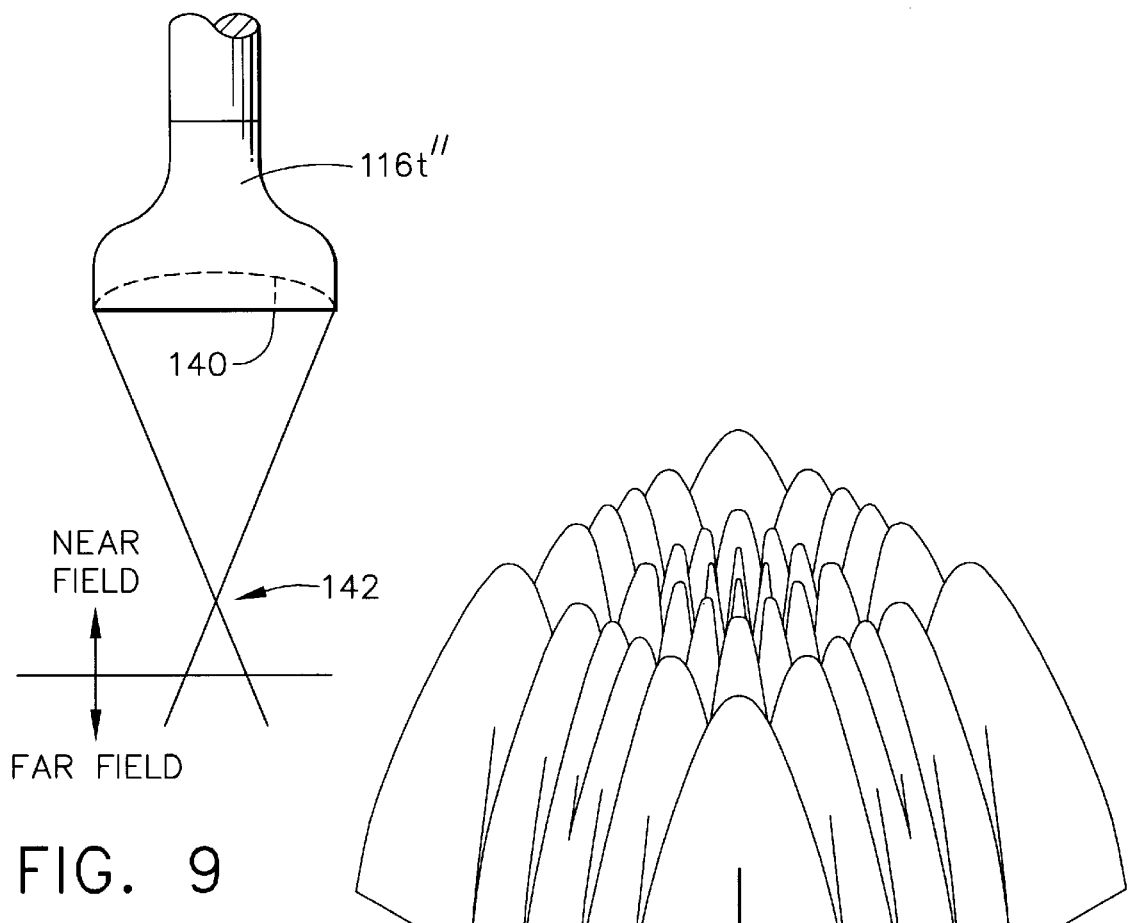
FIG. 9
FIG. 10
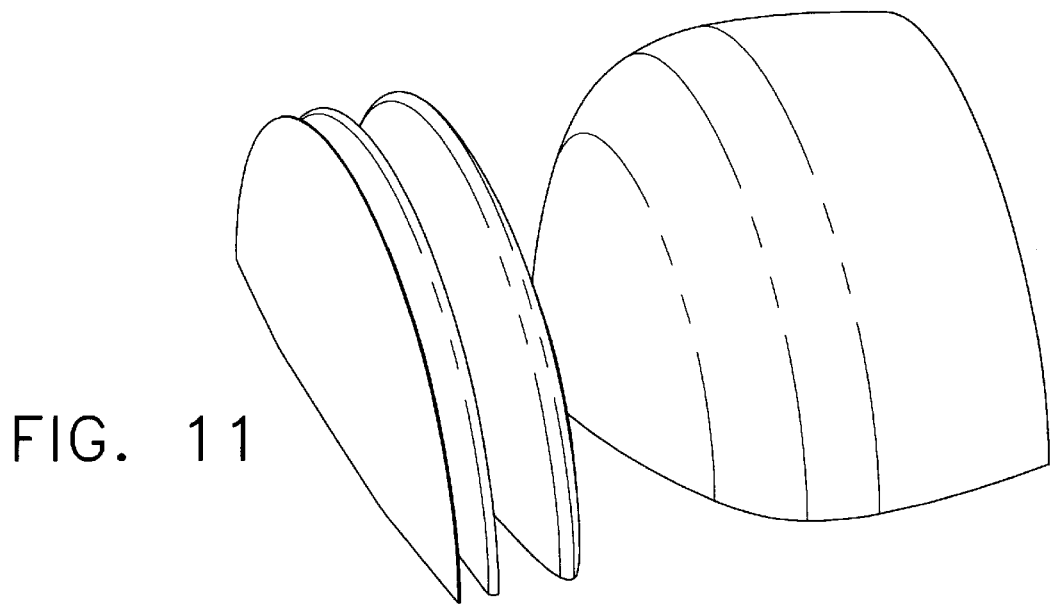
FIG. 11

MEDICAL APPLICATIONS OF ULTRASONIC ENERGY

This is a continuation of application Ser. No. 08/292,711, filed Aug. 18, 1994 now abandoned, which is hereby incorporated by reference.

BACKGROUND OF THE INVENTION

The present invention relates in general to ultrasonic energy and, more particularly, to the application of ultrasonic energy in medical applications to cause nerves to dysfunction without substantially damaging tissues surrounding the nerves and to ultrasonic transducer probes for these medical applications.

It is known to use ultrasound or ultrasonic energy in medical procedures and that ultrasonic energy can be useful in medical procedures performed in proximity to nerves. However, literature on the topic discloses conflicting conclusions. A first school suggests using ultrasonic energy to selectively dissect around nerves describing the ability of ultrasonic energy to remove tissue while sparing nerves associated with the tissue.

A second school reports nerve damage due to ultrasonic energy and specifically mentions nerve damage up to 1.5 mm ahead of an ultrasonic energy applying tip. At this time, it is thus not clear whether and how to apply ultrasonic energy in treating nerves and/or tissues surrounding nerves and what impact such treatment will have on nerves, in the case of tissue treatment, or on tissue, in the case of nerve treatment.

There are a wide variety of instances when it would be desirable to be able to make a given nerve dysfunctional without substantially harming the tissues surrounding or associated with the nerve. Examples include and range from twitches and chronic pain to major surgical procedures such as vagotomies to correct ulcers and the maize procedure to correct heart arrhythmias. Another application would be to open up a blood vessel, either a vein or artery, which has closed due to spasm caused by trauma. Many other applications will be apparent to medical personnel with specialized knowledge of given portions or systems of the body.

It is, thus, apparent that a need exists for a non or minimally invasive procedure for making a given nerve dysfunctional without substantially damaging surrounding tissues.

SUMMARY OF THE INVENTION

This need is met by the invention of the present application wherein ultrasonic energy is used to cause a selected nerve to become dysfunctional without substantially damaging tissues surrounding or associated with the nerve. It is currently preferred to utilize the near field or evanescent field of an ultrasonic wave front for the invention. A nerve to be made dysfunctional is placed in the near field of ultrasonic energy emitted by an appropriately formed ultrasonic transducer probe.

In accordance with one aspect of the present invention, a method of causing nerve dysfunction without substantially damaging surrounding tissue comprises the steps of: locating a nerve which is to be made dysfunctional, positioning an ultrasonic transducer probe adjacent the nerve; and, driving the ultrasonic transducer probe to apply ultrasonic energy to the nerve. The method may further comprise the step of selecting the frequency of the ultrasonic energy to be within the range of 15 kilohertz to 500 kilohertz for energy applications with a contact probe or selecting the frequency to be within the range of 100 kilohertz to 5 megahertz for energy applications with a focused non-contact probe.

The step of driving the ultrasonic transducer probe to apply ultrasonic energy to the nerve may comprise the step of selecting the driving energy such that nerve dysfunction is either permanent or temporary. The method further comprises the step of selecting the driving energy to be within the range of 7 to 240 watts per square centimeter.

The step of positioning an ultrasonic transducer probe adjacent the nerve is currently preferred to comprise the step of sweeping the probe over the nerve in at least one sweep and, for a contact probe, with a substantially constant pressure. The step of positioning an ultrasonic transducer probe adjacent the nerve also preferably comprises the step of placing the probe such that the nerve is within a near field of the ultrasonic energy applied by the probe. However, the step of positioning an ultrasonic transducer probe adjacent the nerve may also comprise the step of placing the probe in contact with the nerve or placing the probe such that the nerve is within 0 to 8 mm from the end of the probe for contact transducer probes and within the near field of focused non-contact probes.

The step of driving the ultrasonic transducer probe to apply ultrasonic energy to the nerve may comprise the step of producing an interference pattern in the near field of the ultrasonic energy applied by the probe with constructive interference peaks being spaced equal to or less than a cross sectional diameter of the nerve. Alternately, the step of driving the ultrasonic probe to apply ultrasonic energy to the nerve may comprise the step of producing an interference pattern in the near field of the ultrasonic energy applied by the probe with constructive interference peaks being spaced greater than or equal to a cross sectional diameter of tissue cells surrounding the nerve.

In accordance with another aspect of the present invention, an ultrasonic drive rod for applying ultrasonic energy to a nerve to cause dysfunction of the nerve without substantially damaging surrounding tissue comprises a proximal end received within a handpiece of an ultrasonic energy generator system. A distal tip end of the drive rod defines an oblong tissue engaging surface. An extension rod interconnects the proximal end and the distal end to set the length of rod as desired. Preferably, the oblong tissue engaging surface of the tip end of the driving rod ranges in width from 2 to 6 mm and ranges in width from 4 to 10 mm. Further, the outer periphery of the oblong tissue engaging surface of the distal tip end of the driving rod is rounded to prevent damaging tissue during the application of ultrasonic energy.

In accordance with yet another aspect of the present invention, an ultrasonic drive rod for applying ultrasonic energy to a nerve to cause dysfunction of the nerve without substantially damaging surrounding tissue comprises a proximal end received within a handpiece of an ultrasonic energy generator system, a distal tip end defining an oblong ultrasonic energy focusing end surface and an extension rod interconnecting the proximal end and the distal end. The oblong ultrasonic energy focusing end surface ranges in width from 2 to 6 mm and ranges in length from 4 to 10 mm.

It is thus an object of the present invention to provide an improved method for causing a given nerve to become dysfunctional without substantially damaging tissues surrounding or associated with the nerve, and to provide an ultrasonic drive rod having an oblong contact or non-contact tip end for use in applying ultrasonic energy for causing nerve dysfunction.

Other objects and advantages of the invention will be apparent from the following description, the accompanying drawings and the appended claims.

BRIEF DESCRIPTION OF THE DRAWINGS

FIG. 9 is a front view of the focused non-contact transducer probe of FIGS. 6a and 6b showing the focused ultrasonic energy emitted therefrom;

FIG. 10 illustrates a near field interference pattern created by a commercially available ultrasonic probe tip; and FIG. 11 illustrates a near field interference pattern for the oblong distal tip ends of the driving rods illustrated with reference to FIGS. 1–4c and 6a–9.

DETAILED DESCRIPTION OF THE INVENTION

Figure 1:
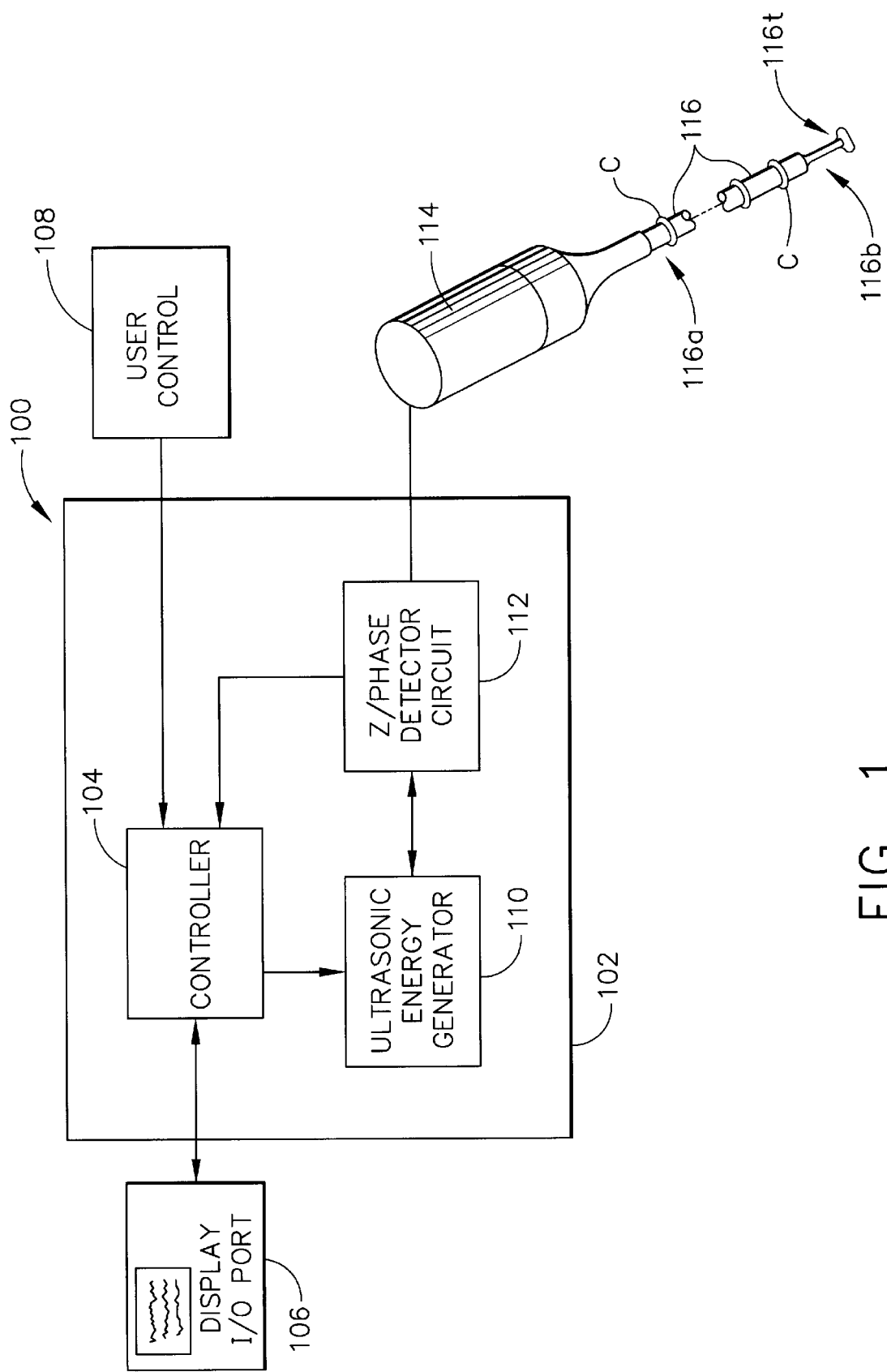
FIG. 1 is a schematic block diagram of an ultrasonic surgical system operable in accordance with one aspect of the present invention.
Figure 2:
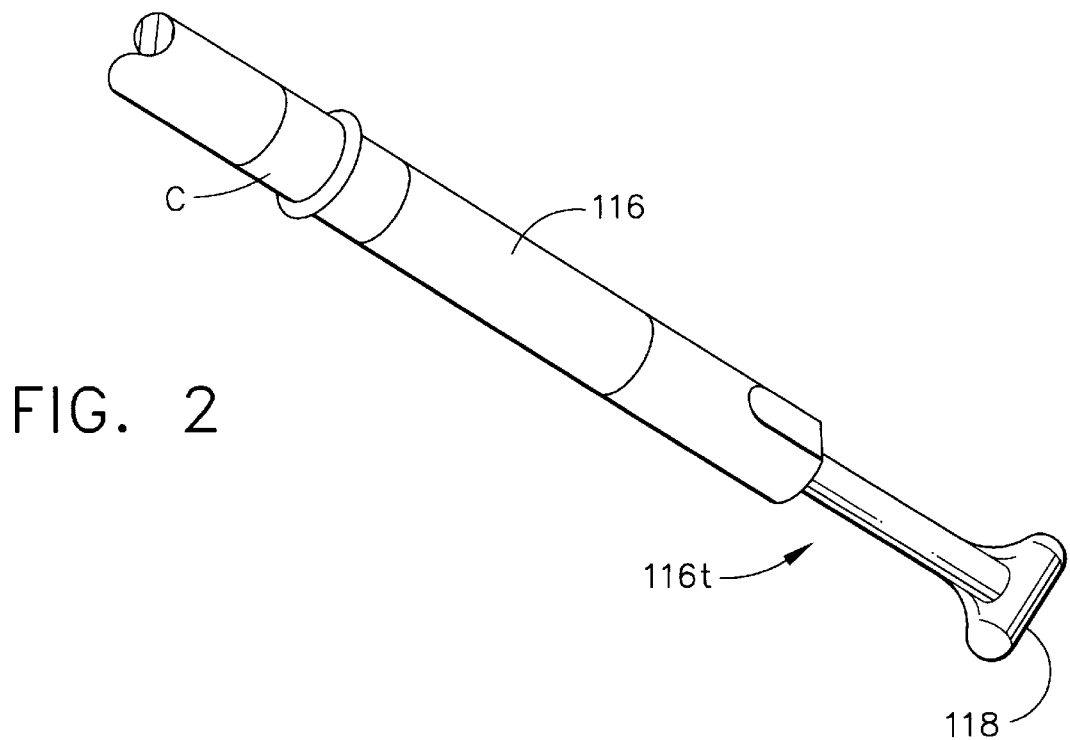
FIG. 2 is a perspective view of a distal tip end of a driving rod in accordance with a second aspect of the present invention.
Figure 3A:
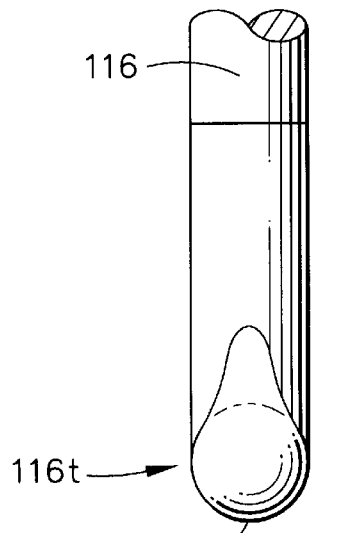
FIGS. 3a–3c show side, front and bottom views of the distal tip end of the driving rod of FIG. 2.
Figure 3B:
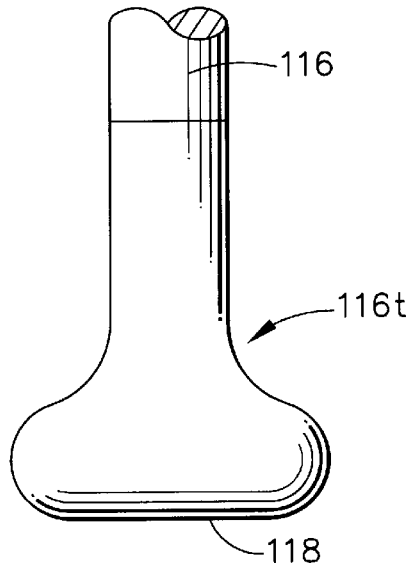
Figure 3C:
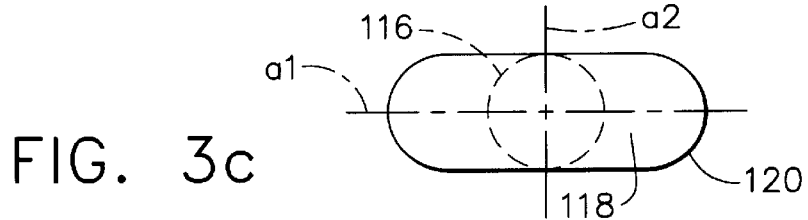

The invention of the present application will now be described with reference to the drawing figures. An ultrasonic surgical system 100 is illustrated in FIG. 1. The ultrasonic surgical system 100 comprises a primary ultrasonic energy source 102 which includes a controller 104 which is coupled to a display and input/output (I/O) port circuit 106 and a user control circuit 108. The controller 104 is also coupled to an ultrasonic energy generator 110 and an impedance (Z)/phase detector circuit 112, for example, a phase locked loop circuit may be employed for the Z/phase detector circuit 112. The Z/phase detector circuit is connected to a handpiece 114 which receives a proximal end 116a of a driving rod 116. The distal tip end 116b of the driving rod 116 is terminated in an interchangeable tissue engaging tip 116t.

A variety of ultrasonic surgical systems are commercially available for performing various surgical applications including cutting and coagulating tissue. UltraCision Incorporated is an example of a source of ultrasonic surgical systems, such as the system illustrated in FIG. 1. These commercially available systems include a variety of ultrasonic driving rods which can be utilized in the systems. However, the illustrated driving rod 116 is constructed in accordance with one of the aspects of the present invention and is more clearly illustrated in and will be described with reference to FIGS. 2–4c.

The driving rod 116 of the present invention includes a proximal end received within the handpiece 114 of an ultrasonic energy generator system, such as the ultrasonic surgical system 100 illustrated in FIG. 1. The driving rod 116 includes a series of resilient support collars c which center the driving rod within a support tube (not shown) in a conventional manner. For certain operations performed in accordance with the present invention, the distal tip end 116t comprises a tissue engaging tip 116t' defining an oblong tissue engaging surface 118 illustrated in FIGS. 2–5. The oblong tissue engaging surface 118 ranges in length from 4 to 10 mm along long axis a1 and ranges in width from 2 to 6 mm along the short axis a2. The outer periphery 120 of the oblong tissue engaging surface 118 of the distal tip end 116t' is rounded to prevent damaging tissue during the application of ultrasonic energy.

Figure 4A:
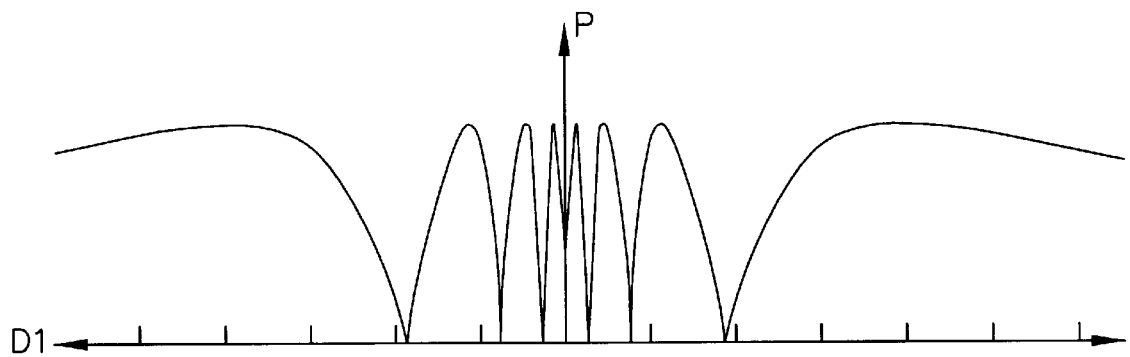
FIGS. 4a–4c show power versus distance graphs for ultrasonic energy emitted from the distal tip end of the driving rod of FIGS. 1–3c.
Figure 4B:
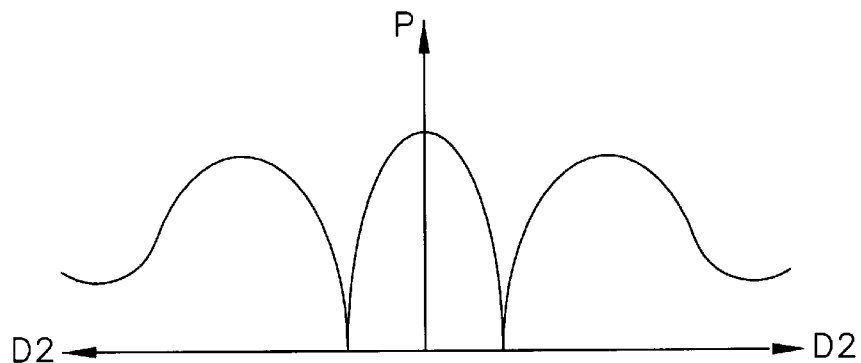
Figure 4C:
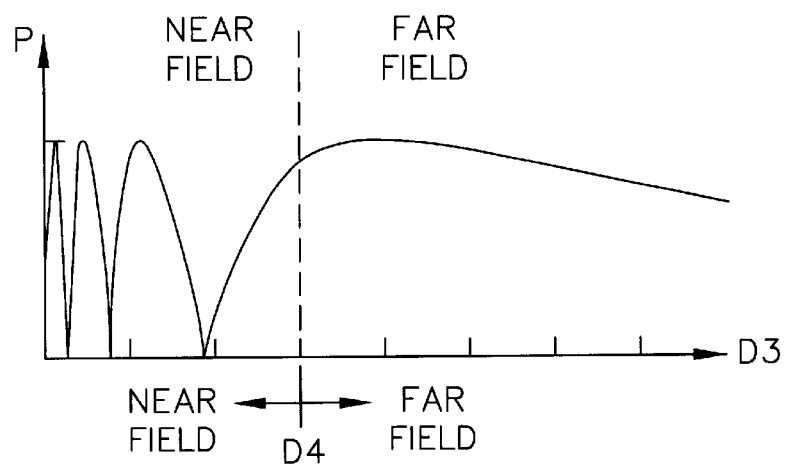

FIGS. 4a–4c illustrate normalized pressures created by ultrasonic energy when the ultrasonic surgical system 100 is operated with the distal tip end 116t' in place. In particular, FIG. 4a illustrates ultrasonic pressure P induced along the long axis a1 of the oblong tissue engaging surface 118 versus distance D1 along the long axis a1; FIG. 4b illustrates ultrasonic pressure P induced along the short axis a2 of the oblong tissue engaging surface 118 versus distance D2 along the short axis a2; and, FIG. 4c illustrates the ultrasonic pressure P versus the longitudinal distance D3 from the distal tip end 116t' of the driving rod 116.

Ultrasonic energy fields are divided into a near or evanescent field and a far field. As illustrated in FIG. 4c, the near field is generally considered to be within a distance D4 from the distal tip end 116t' of the driving rod 116 while the far field is generally considered to be beyond the distance D4 from the distal tip end 116t' of the driving rod 116.

For a rounded tip end, the ultrasonic pressures result in interference patterns within the near field which are generally represented by FIG. 10. For the oblong distal tip end 116t' illustrated in FIGS. 2–5, the interference pattern is concentrated along the long axis a1 as illustrated in FIG. 11.

While the present invention is generally applicable to a wide variety of medical applications, it will be described herein with primary reference to endoscopic performance of a vagotomy operation utilizing ultrasonic energy. Since the vagotomy operation is well known to surgeons and other related medical personnel having skill in the art, having been performed both conventionally since 1943 and endoscopically in more recent times, the specifics of the vagotomy operation will be described herein only to the extent necessary for an understanding of the present invention.

Figure 5:
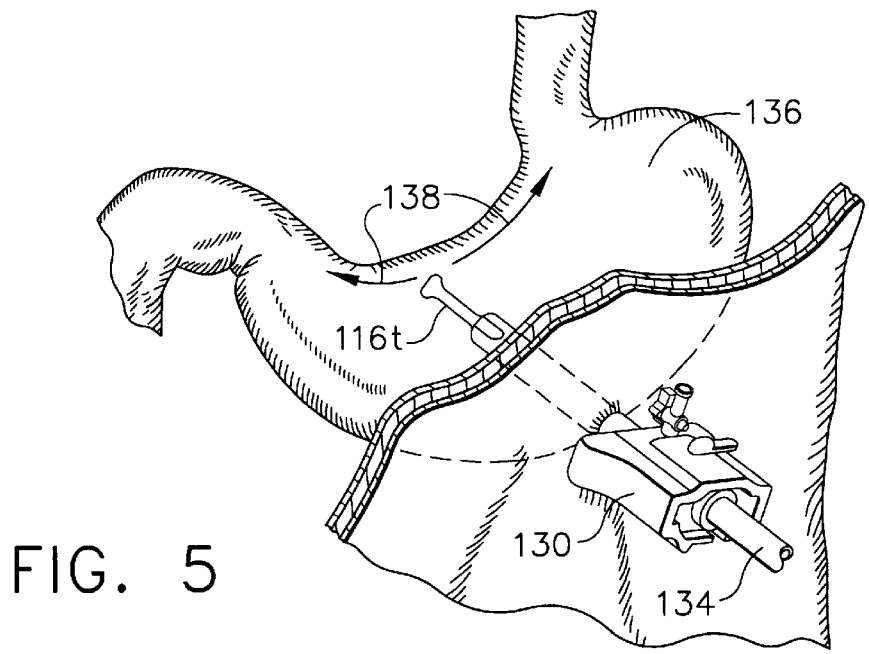
FIG. 5 is a perspective view of an application of the present invention to perform a vagotomy operation.
Figure 6A:
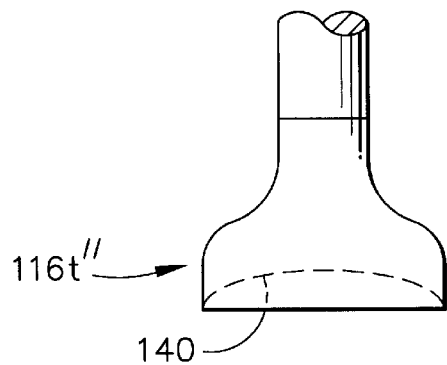
FIGS. 6a and 6b show front and bottom views of the distal end of a focused non-contact transducer probe.
Figure 7:
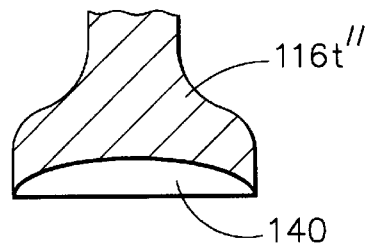
FIG. 7 is a sectional view of the tip end of the focused non-contact transducer probe of FIGS. 6a and 6b taken along the section line 7—7.
Figure 6B:
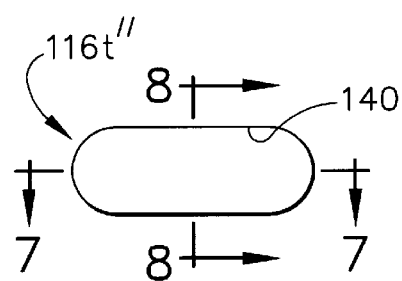
Figure 8:
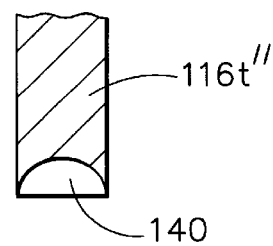
FIG. 8 is a sectional view of the tip end of the focused non-contact transducer probe of FIGS. 6a and 6b taken along the section line 8—8.

As shown in FIG. 5, an abdominal wall 130 has been penetrated by a trocar 132 through which an ultrasonic probe 134 is inserted. The probe 134 includes the driving rod 116 which terminates in the distal tip end 116t'. The surgeon performing the vagotomy observes the positioning of the distal tip end 116t' along the lesser curve of the stomach 136 to follow the path generally outlined by the arcuate arrows 138. The ultrasonic energy, which can range in frequency from 15 kilohertz to 500 kilohertz and in power level between 7 watts per square meter and 240 watts per square centimeter, is selected such that nerve dysfunction occurs.

The operation is performed by sweeping the ultrasonic probe 134 over the nerve in at least one sweep with the number of sweeps depending upon the particular operation being performed and also the ultrasonic power level selected. Preferably, the probe 134 is maintained in engagement with the tissue overlying the nerve with a substantially constant pressure.

In other operations, the probe 134 may be placed in contact with the nerve to be made dysfunctional, placed such that the nerve is within 0 to 8 mm from the end of the probe 134, or placed such that the nerve is within a near or evanescent field of the ultrasonic energy applied by the probe 134.

Permanent nerve dysfunction is desired in many procedures including and ranging from twitches and chronic pain to major surgical procedures such as vagotomies and the maize procedure to correct heart arrhythmias. Another application is to open up a blood vessel, either a vein or artery, which has closed due to spasm caused by trauma or occlusion from plaque. Many other applications will be apparent to medical personnel with specialized knowledge of given portions or systems of the body. Temporary nerve dysfunction is desired in other procedures, for example for use as an anaesthetic.

For certain operations performed in accordance with the present invention, the distal tip end 116t'' comprises a focused non-contact tip 116t'' defining an oblong ultrasonic energy focusing surface 140 illustrated in FIGS. 6a–9. The oblong focusing surface 140 ranges in length from 4 to 10 mm along its long axis which coincides with the section line 7—7 and ranges in width from 2 to 6 mm along its short axis which coincides with section line 8—8.

As shown in FIG. 9, the distal tip end 116t'' focuses the ultrasonic energy with a strong interference zone resulting at the focus point 142 within the near field of the focused ultrasonic energy. Probes including the distal tip end 116t'' are constructed utilizing well known techniques which are in accordance with optical focusing techniques such that the focusing surface 140 forms a portion of a parabolic surface. Other probes having focused non-contact tips are commercially available, for example, tips having a concave spherically surface are known and can be used in accordance with the broad aspects of the present invention.

Probes having focused non-contact tips can be used extracorporeally with the application of the ultrasonic energy being directed by non-interfering ultrasonic scanning devices which are associated with the probes. Such non-contact applications of ultrasonic energy is currently being clinically used for conventional medical treatments and its extension to the invention of the present application will be apparent to those skilled in the art in view of the forgoing disclosure.

Having thus described the invention of the present application in detail and by reference to preferred embodiments thereof, it will be apparent that modifications and variations are possible without departing from the scope of the invention defined in the appended claims.

What is claimed is:

1. A method of causing nerve dysfunction without substantially damaging surrounding tissue, said method comprising the steps of:

locating a nerve which is to be made dysfunctional;

sweeping an ultrasonic probe over said nerve in at least one sweep such that said nerve is within a near field of ultrasonic energy applied by said probe; and driving said ultrasonic probe to apply said ultrasonic energy to said nerve by producing an interference pattern in the near field of the ultrasonic energy applied by said probe with constructive interference peaks being spaced equal to or less than a cross sectional diameter of said nerve.

2. A method of causing nerve dysfunction without substantially damaging surrounding tissue, said method comprising the steps of:

locating a nerve which is to be made dysfunctional;

touching an ultrasonic probe to tissue overlying said nerve such that said nerve is within a near field of ultrasonic energy applied to said probe; and driving said ultrasonic probe to apply said ultrasonic energy to said nerve by producing an interference pattern in the near field of the ultrasonic energy applied by said probe with constructive interference peaks being spaced equal to or less than a cross sectional diameter of said nerve.

3. A method of causing nerve dysfunction without substantially damaging surrounding tissue, said method comprising the steps of:

locating a nerve which is to be made dysfunctional;

sweeping an ultrasonic probe over said nerve in at least one sweep such that said nerve is within a near field of the ultrasonic energy applied by said probe; and driving said ultrasonic probe to apply said ultrasonic energy to said nerve producing an interference pattern in the near field of the ultrasonic energy applied by said probe with constructive interference peaks being spaced greater than or equal to a cross sectional diameter of tissue cells surrounding said nerve.

4. A method of causing nerve dysfunction without substantially damaging surrounding tissue, said method comprising the steps of:

locating a nerve which is to be made dysfunctional;

touching an ultrasonic probe to tissue overlying said nerve such that said nerve is within a near field of ultrasonic energy applied by said probe; and driving said ultrasonic probe to apply said ultrasonic energy to said nerve by producing an interference pattern in the near field of the ultrasonic energy applied by said probe with constructive interference peaks being spaced greater than or equal to a cross sectional diameter of tissue cells surrounding said nerve.

5. A method of causing nerve dysfunction without substantially damaging surrounding tissue, said method comprising the steps of:

locating a nerve which is to be made dysfunctional;

positioning an ultrasonic probe adjacent said nerve by touching said probe to tissue overlying said nerve such that said nerve is within a near field of ultrasonic energy applied to said probe;

sweeping said probe over said nerve in at least one sweep; and driving said ultrasonic probe to apply ultrasonic energy to said nerve by producing an interference pattern in the near field of the ultrasonic energy applied by said probe with constructive interference peaks being spaced equal to or less than a cross sectional diameter of said nerve.

6. A method of causing nerve dysfunction without substantially damaging surrounding tissue, said method comprising the steps of:

locating a nerve which is to be made dysfunctional;

positioning an ultrasonic probe adjacent said nerve by touching said probe to tissue overlying said nerve such that said nerve is within a near field of ultrasonic energy applied by said probe;

sweeping said probe over said nerve in at least one sweep; and driving said ultrasonic probe to apply said ultrasonic energy to said nerve by producing an interference pattern in the near field of the ultrasonic energy applied by said probe with constructive interference peaks being spaced greater than or equal to a cross sectional diameter of tissue cells surrounding said nerve.

* * * * *